(12) United States Patent
Huo et al.

(10) Patent No.: US 9,512,450 B1
(45) Date of Patent: Dec. 6, 2016

(54) MICROBIAL PRODUCTION OF FUEL COMPONENTS FROM LOW-MOLECULAR WEIGHT GAS MIXTURES

(71) Applicant: Easel Biotechnologies, LLC, Culver City, CA (US)

(72) Inventors: Yi-Xin Huo, Los Angeles, CA (US); Lars Erik Ulf Rohlin, Los Angeles, CA (US); Shahrooz Rabizadeh, Los Angeles, CA (US)

(73) Assignee: Easel Biotechnologies, LLC, Culver City, CA (US)

( * ) Notice: Subject to any disclaimer, the term of this patent is extended or adjusted under 35 U.S.C. 154(b) by 0 days.

(21) Appl. No.: 14/187,465

(22) Filed: Feb. 24, 2014

Related U.S. Application Data

(60) Provisional application No. 61/768,152, filed on Feb. 22, 2013.

(51) Int. Cl.
  *C12P 7/06* (2006.01)
  *C12N 9/20* (2006.01)
  *C12P 7/24* (2006.01)
  *C12N 15/74* (2006.01)

(52) U.S. Cl.
  CPC ............ *C12P 7/24* (2013.01); *C12N 15/74* (2013.01)

(58) Field of Classification Search
  None
  See application file for complete search history.

(56) References Cited

PUBLICATIONS

Hanson et al (Methanotrophic Bacteria, Microbiological Reviews, Jun. 1996, p. 439-471,(American Society for Microbiology).*
Production of Methanol from Methane by Methanotrophic Bacteria Biocatalysis and Biotransformation, 2004 vol. 22 (3). pp. 225 229.*
Hollaender et al (Genetic Engineering of Microorganisms for Chemicals, 383-402, 1982).*

\* cited by examiner

*Primary Examiner* — Kagnew H Gebreyesus
(74) *Attorney, Agent, or Firm* — Fish & Tsang, LLP

(57) ABSTRACT

Systems, methods, and metabolically engineered microorganisms are contemplated in which low molecular weight gases, and especially methane and syngas are used as a carbon source, and in which $CO_2$ or formaldehyde and reduction equivalents are generated for use in in vivo production of the value products.

9 Claims, 12 Drawing Sheets

A: Methane Monooxygenase;  B: alcohol oxidase;  C: formaldehyde dismutase

Ralstonia own alcohol dehydrogenase may replace enzyme B.

MICROBIAL PRODUCTION OF FUEL COMPONENTS FROM LOW-MOLECULAR WEIGHT GAS MIXTURES

This application claims priority to U.S. provisional application Ser. No. 61/768,152, which was filed Feb. 22, 2014, which is incorporated by reference herein.

FIELD OF THE INVENTION

The field of the invention is use of energetic low-molecular weight gas mixtures, and especially syngas and/or methane as feedstock for microbial production of fuel components, particularly alcohols, aldehydes, and/or acids.

BACKGROUND OF THE INVENTION

Microbial production of various biofuel components is well known in the art and may use isolated naturally occurring microorganisms, or genetically engineered microorganisms that have one or more genes added or modified/deleted to improve product yield.

For example, GB2018822B teaches use of methylotrophic bacteria to produce various hydrocarbon products from methane as feedstock. While such methods advantageously allow use of aerobic culture conditions, yields are often less than desirable and the culture medium typically requires the presence of one or more methyl-radical donating carbon-containing compounds.

In other examples, anaerobic bacteria have been used to convert carbon monoxide to alcohols, including butanol, ethanol, and acetic acid, and typical microorganisms include those of the genus *Clostridium* (e.g., *Clostridium lungdahlii*, including those described in WO 00/68407, EP 117309, U.S. Pat. Nos. 5,173,429, 5,593,886, and 6,368,819, WO 98/00558 and WO 02/08438, and *Clostridium autoethanogenum* (Aribini et al, Archives of Microbiology 161: pp 345-351)). Other Clostridial species using syngas are described in US 2010/0203606 and 2007/0275447 for production of ethanol from carbon monoxide. Further suitable bacteria include those of the genus *Moorella*, including *Moorella* sp HUC22-1, (Sakai et al, Biotechnology Letters 29: pp 1607-1612), and those of the genus *Carboxydothermus* (Svetlichny, V. A., Sokolova, T. G. et al (1991), Systematic and Applied Microbiology 14: 254-260). However, the media composition in many cases is relatively complex, and culture conditions are often difficult to reproduce.

To reduce complexity for media, carbon dioxide may be added to the medium while maintaining free acid concentration below a threshold value to so improve production flow as previously shown in WO2009/114127 where selected (typically Clostridial) microorganisms produce ethanol using syngas as a feedstock. However, anaerobic culture conditions must be maintained during the fermentation in most cases, which will once more increase operational complexity. Further media modifications are described in US 2011/0236919 in which a surface tension active compound is used to control quantities of the dissolved gases.

Likewise, WO 2011/139804 describes various hybrid production processes in which oxyhydrogen microorganisms (and in particular purple non-sulfur photosynthetic bacteria) are employed for non-photosynthetic carbon capture and conversion of inorganic and/or C1 carbon sources into useful organic compounds. However, the production set-up for biofuel components in this process is yet again relatively complex.

Thus, there is still a need to provide improved systems and methods for production of biofuel components, and particularly alcohols, aldehydes, and acids using microorganisms in a conceptually simple and effective manner using low-molecular weight gases and mixtures thereof.

SUMMARY OF THE INVENTION

The inventive subject matter is directed to cells, methods, and culture conditions for microbial strains and genetically modified microbial strains to generate from low-molecular weight gases in a conceptually simple manner various biofuel components, and particularly short- and mid-chain alcohols, aldehydes, and carboxylic acids.

In one aspect of the inventive subject matter, a method of producing a value product that includes a step of providing syngas or methane, and using a microorganism to convert the syngas or methane into reduction equivalents and at least one of $CO_2$ and formaldehyde, and a further step of using a CBB cycle, a serine cycle, or a RuMP cycle in the microorganism to produce the value product.

In some aspects of the inventive subject matter, the microorganism is genetically modified to convert CO from syngas into $CO_2$ and to generate the reduction equivalents during the conversion of the CO to $CO_2$. For example, the genetic modification may include a recombinant gene that encodes an enzyme having CO reductase activity, and optionally a recombinant gene that encodes an enzyme having hydrogenase activity. In other aspects, the microorganism is genetically modified to convert methane into formaldehyde and to generate the reduction equivalents during the conversion of the methane to the formaldehyde. For example, such genetic modification may include one or more recombinant genes that encode an enzyme having an activity selected from the group consisting of methane monooxygenase, alcohol dehydrogenase, and formaldehyde dismutase. In still further aspects, the microorganism may also be genetically modified to convert methane into $CO_2$ and to generate the reduction equivalents during the conversion of the methane to the formaldehyde. For example, such genetic modifications may include at least one recombinant gene that encodes an enzyme having an activity selected from the group consisting of factor F420-reducing hydrogenase, F420-dependent methylene-H4SPT dehydrogenase, heterodisulfide reductase, methyl-coenzyme M reductase, methyl-H4MPT:coenzyme M methyltransferase complex, F420-dependent methylene-H4SPT reductase, 5,6,7,8-tetrahydromethanopterin hydro-lyase (formaldehyde-activating enzyme), and formaldehyde dehydrogenase.

In still further contemplated aspects, the microorganism may also be genetically modified to have at least one recombinant gene in the CBB cycle, the serine cycle, or the RuMP cycle. For example, the recombinant gene in the CBB cycle encodes a protein having phosphoribulokinase activity or phosphoketolase activity. Additionally, it is contemplated that the microorganism may be genetically modified to have reduced or abrogated activity for at least one of aldehydes dehydrogenase and alcohol dehydrogenase. Thus, especially preferred value product include an aldehydes (e.g., butyraldehyde).

While not limiting to the inventive subject matter, the microorganism may be an aerobic microorganism (e.g., belonging to the genus of *Ralstonia*), that is cultivated under aerobic conditions. Alternatively, the microorganism may also be an aerobic microorganism that is genetically modified to grow under anaerobic conditions.

Therefore, the inventor also contemplates a genetically engineered microorganism that comprises a plurality of genes to provide enzymatic functions for (a) conversion of syngas or methane into reduction equivalents and at least one of $CO_2$ and formaldehyde, and (b) C1 assimilation via $CO_2$ or formaldehyde, using a CBB cycle, a serine cycle, or a RuMP cycle, wherein the microorganism is genetically modified to express at least one of the enzymatic functions from a recombinant gene.

Most typically, the genetic modification is at least one of (a) a recombinant gene that encodes an enzyme having CO reductase activity, (b) a recombinant gene that encodes an enzyme having hydrogenase activity, (c) a recombinant gene that encodes an enzyme having methane monooxygenase activity, (d) a recombinant gene that encodes an enzyme having alcohol dehydrogenase activity, (e) a recombinant gene that encodes an enzyme having formaldehyde dismutase activity, and (f) a recombinant gene that encodes an enzyme having an activity selected from the group consisting of factor F420-reducing hydrogenase, F420-dependent methylene-H4SPT dehydrogenase, heterodisulfide reductase, methyl-coenzyme M reductase, methyl-H4MPT:coenzyme M methyltransferase complex, F420-dependent methylene-H4SPT reductase, 5,6,7,8-tetrahydromethanopterin hydro-lyase (formaldehyde-activating enzyme), and formaldehyde dehydrogenase.

While not limiting to the inventive subject matter, the microorganism is further modified to have a reduced aldehyde dehydrogenase activity, and will preferably belong to the genus of *Ralstonia*.

Various objects, features, aspects and advantages of the present invention will become more apparent from the following detailed description of preferred embodiments of the invention.

DETAILED DESCRIPTION

The inventor discovered that various microorganisms can be genetically modified for microbial synthesis of numerous biofuel components, and especially alcohols, aldehydes, and acids (e.g., keto-acids and hydroxy-acids) from energetic low-molecular weight gases and gas mixtures. In especially preferred aspects, the microorganism is strictly aerobic (e.g., member of the genus *Ralstonia*) and is in at least some aspects genetically modified to allow for an increased yield of short- and mid-chain alcohols, aldehydes, and carboxylic acids.

For example, particularly preferred processes and microorganisms are those that allow for production of ethanol, C3 alcohols and/or C3 aldehydes, C4-C5 alcohols and/or C4-C5 aldehydes, and/or C6-C8 alcohols and/or C6-C8 aldehydes, or polymeric compounds (e.g., polyhydroxyalkanoates) using syngas or methane as carbon source. Most preferably, the microorganisms are strict aerobic microorganisms, and especially belong to the genus *Ralstonia*. In other aspects of the inventive subject matter, a microorganism belonging to the genus *Ralstonia* is genetically modified to allow growth and value product production under anaerobic conditions. Thus, it should be noted that methods and microorganisms according to the inventive subject matter can be used to prepare numerous renewable value-added compounds from (shifted or raw) syngas or methane.

Figure 1:
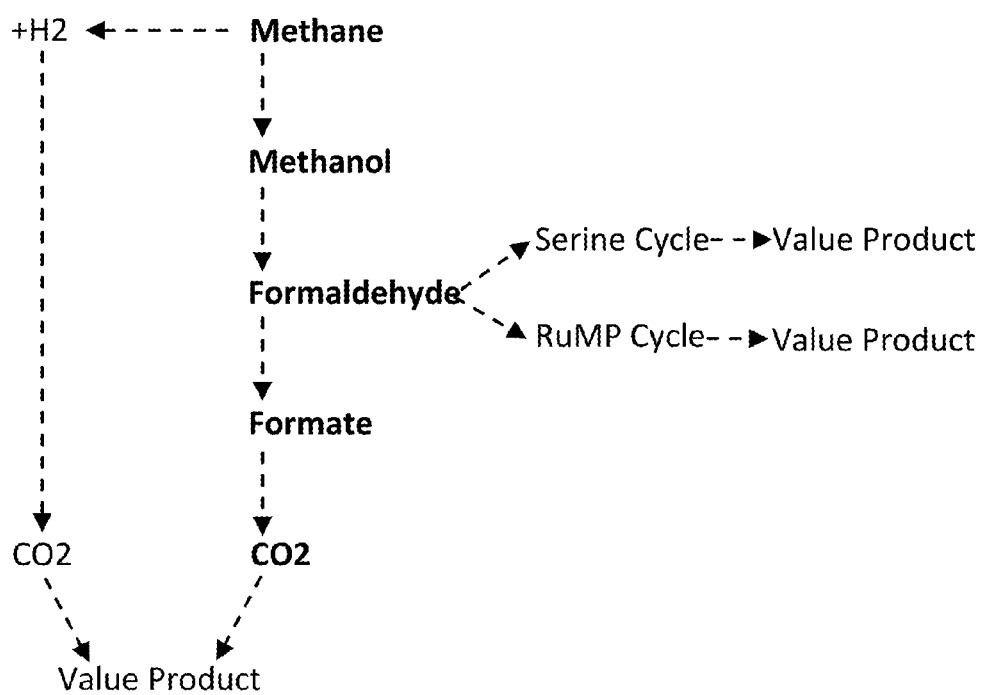
FIG. 1 is a general exemplary schematic of contemplated systems and methods for production of a value product from low-molecular weight materials, and especially from methane and syngas.

In the simplified schematic of FIG. 1, contemplated pathways and routes are shown through which various value products are produced. Here, methane is oxidized through various stages (methanol, formaldehyde, formate) to ultimately form $CO_2$ with concurrent production of reduction equivalents (not shown here). Such step-wise oxidation can be performed entirely in vivo, or at least in part ex vivo using chemical conversion processes well known in the art, and intermediate oxidation products (and especially formaldehyde) are then employed to feed metabolic pathways leading to value product production. Of course, it should be appreciated that these pathways may already be present in a cell or be engineered pathways by expression of enzymes in a cell to provide the specific enzymatic activities. On the other hand, methane can also be subjected to steam reforming to so produce raw syngas that can be employed as a feed as shown in further detail below. Of course, it should be appreciated that the syngas need not be derived from methane reforming, but may also be obtained from numerous other processes that produce syngas as predominant product (e.g., gasification of biomass, lignocellulosic materials, etc., steamhydrogasification of coal or biomass) or byproduct (e.g., recycle or waste gas in gasification or steamhydrogasification). Moreover, the methane used in contemplated systems and processes need not be chemically pure (e.g., >99 mol %), but may be a component of raw natural gas (and as such be in combination with ethane, natural gas liquids, and/or BTX) or pipeline gas.

Figure 2A:
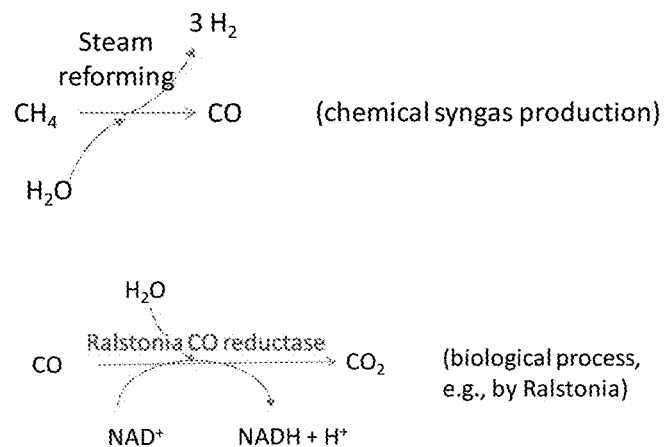
FIGS. 2A and 2B are exemplary schematics for ex vivo conversion of methane to syngas via steam reforming, and in vivo conversion of syngas to $CO_2$ and reduction equivalents.
Figure 2B:
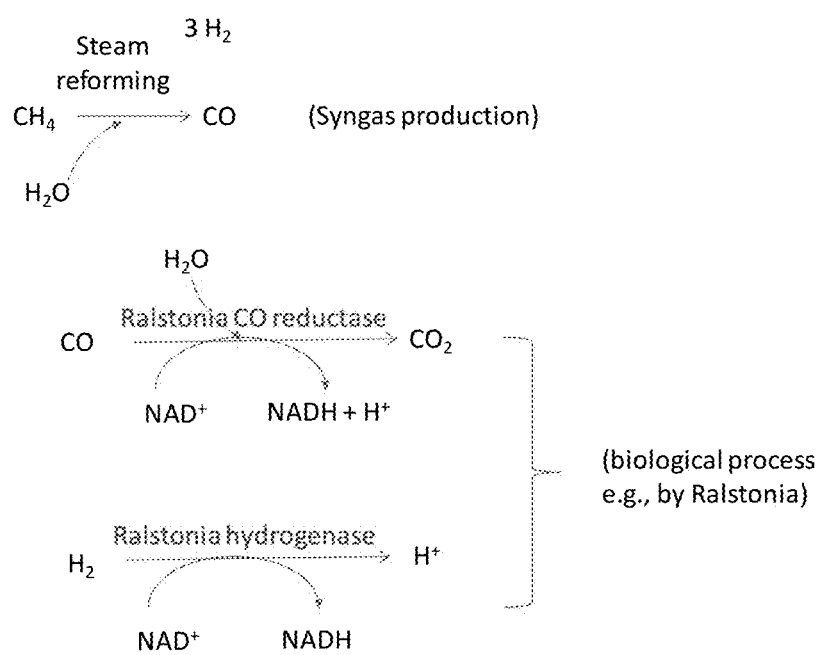

For example, where methane is used as a carbon feed stock, the methane may first be converted to syngas via steam reformation forming a stream comprising $H_2$ and CO. In some instances, the $H_2$ will be used in the production of other value chemicals or as energy source and as such CO will be available as the feedstock for the microbial conversion of CO to $CO_2$ in which advantageously reduction equivalents are being produced. As used herein, the term "reduction equivalents" refers to molecular entities that are used as cofactors in biological redox processes. Thus, the term "reduction equivalents" especially includes NADH, NADPH, FADH, Ferredoxin, coenzyme F420, and FMNH. For example, FIG. 2A schematically illustrates such process where methane is subjected to ex vivo steam reforming to produce CO and $3H_2$. The so formed CO is then used as a gaseous feedstock for in vivo conversion to $CO_2$ (e.g., in *Ralstonia* spec.), which generates NADH as reduction equivalent, while $H_2$ is used in a different process. Most preferably, the microorganism will have a native or recombinant enzyme suitable for oxidation of CO to $CO_2$ (e.g., using CO reductase). On the other hand, it should be appreciated that at least some of the $H_2$ produced in the steam reformation can also be fed to the in vivo conversion process to generate more reduction equivalents as schematically illustrated in FIG. 2B. Here, methane is again subjected to ex vivo steam reforming to produce CO and $3H_2$. Both, CO and $H_2$ are used as gaseous feedstock for in vivo conversion to $CO_2$ (e.g., in *Ralstonia* spec.) generating NADH as reduction equivalent, while $H_2$ is used to generate reduction equivalents (e.g., NADH via endogenous or recombinant hydrogenase).

Figure 3A:
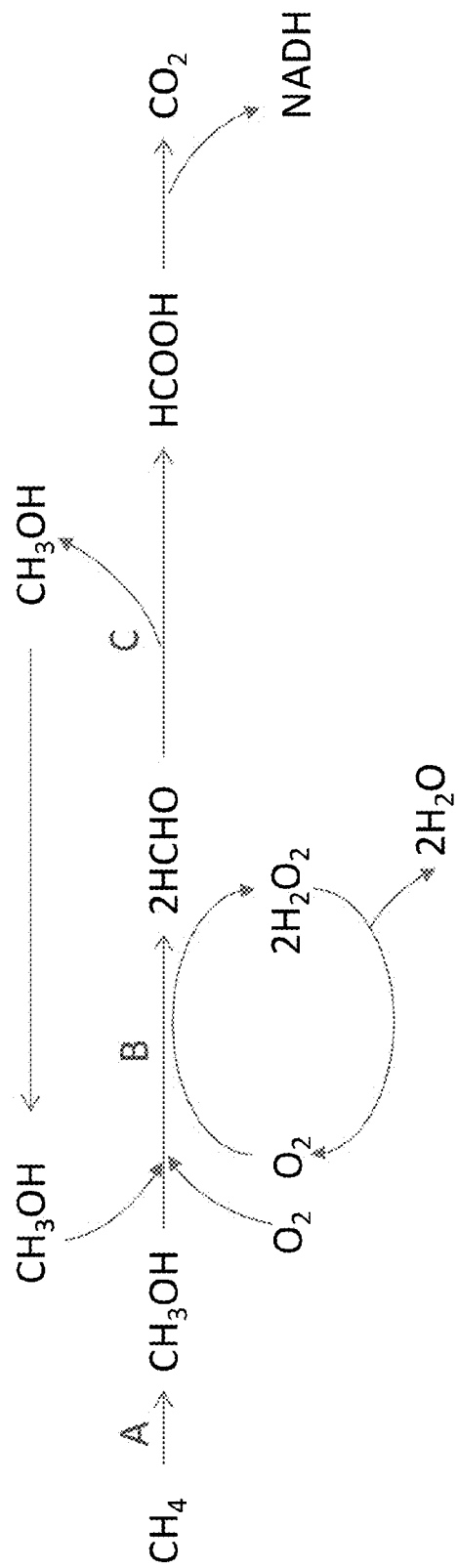
FIGS. 3A-3C are exemplary schematics for in vivo oxidation of methane to $CO_2$ and production of reduction equivalents.
Figure 3B:
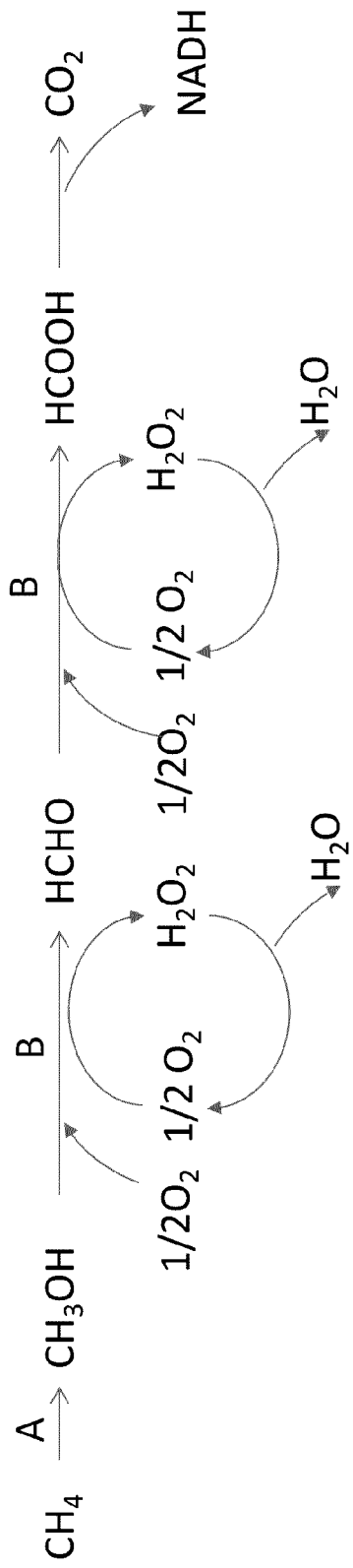
Figure 3C:
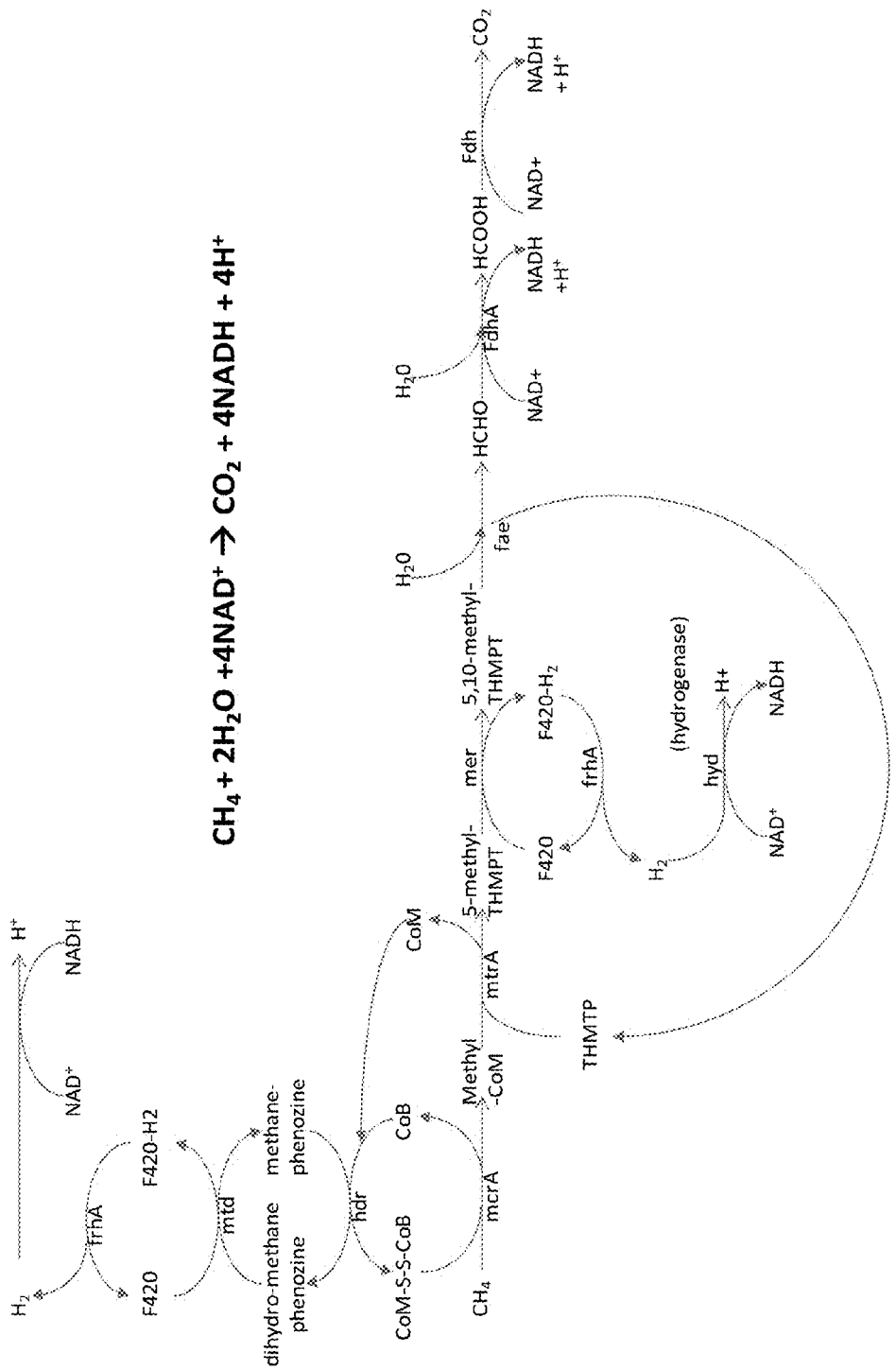

In still further contemplated aspects, and as already noted above, the methane need not necessarily be subjected to a reformation reaction but may also be directly employed as a feedstock. In such case, a microorganism may use (or genetically modified to use) a methane monooxygenase to convert methane to methanol, which may then be further converted via an alcohol oxidase to produce formaldehyde. The so formed formaldehyde may be routed to various other metabolic pathways as further described below, or serve as a substrate for enzymatic conversion to formic acid and further conversion of formic acid to $CO_2$ plus reduction equivalents as exemplarily depicted in FIG. 3A (the last step in the conversion can be performed using various enzymes (e.g., *P. oxalaticus* formate dehydrogenase and *A. eutrophus* hydrogenase). Alternatively, as schematically illustrated in FIG. 3B, the enzymatic conversion of methane to formic acid may be performed with methane monooxygenase and alcohol dehydrogenase/alcohol oxidase, followed by enzymatic conversion of formic acid to $CO_2$ and reduction equivalents. Thus, it should be recognized that microorganisms can be used and/or engineered to convert methane and/or syngas to $CO_2$ and reduction equivalents, where the $CO_2$ and reduction equivalents will be used to generate value products as further described in more detail below.

Where maximization of reduction equivalents is particularly desirable, syngas can be used as a feedstock for a microorganism that has or is modified to have a methane oxidation pathway as exemplarily indicated in FIG. 3C. Here, methane is oxidized to $CO_2$ while yielding 4 mole of reduction equivalent per mole of methane. Molecular hydrogen is used to generate NADH using two separate hydrogenase reactions, one formate dehydrogenase reaction to produce formic acid (e.g., via fdhA) and one formate dehydrogenase reaction to produce $CO_2$ from formate (e.g., via fdhH). The remaining supporting reactions are indicated with the corresponding enzymatic activities/gene names and/or cofactors.

Figure 4A:
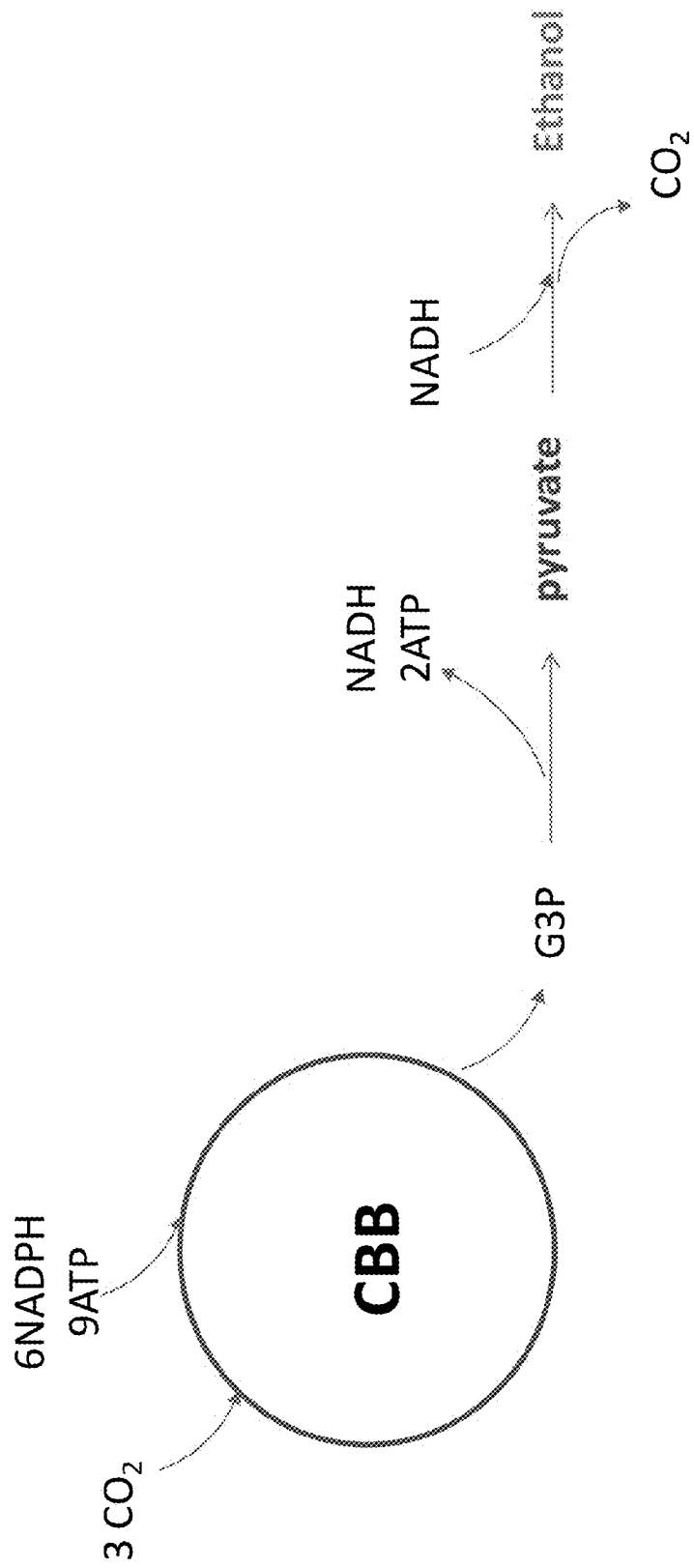
FIGS. 4A and 4B are exemplary schematics for fixation of $CO_2$ using reduction equivalents in the CBB cycle for production of various value products.
Figure 4B:
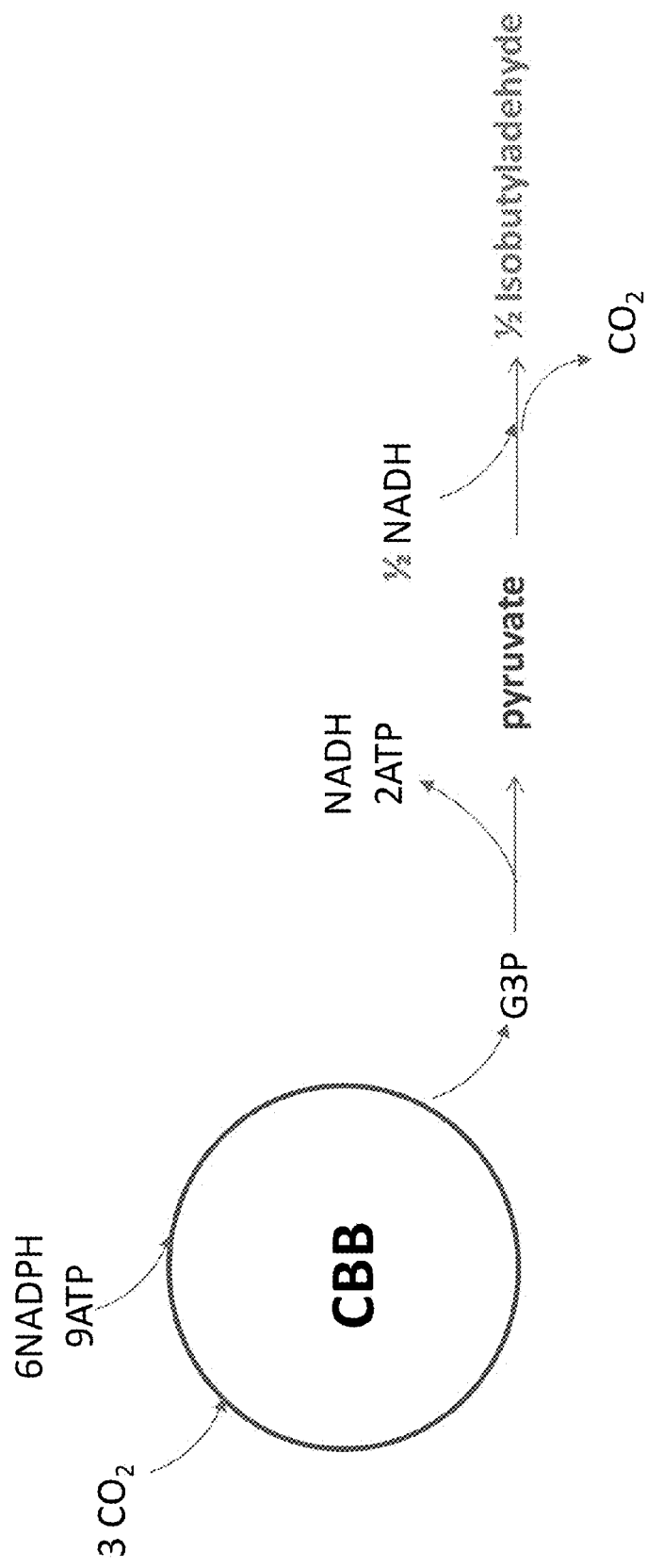

In further contemplated aspects of the inventive subject matter, it should be appreciated that the so generated $CO_2$ and reduction equivalents can be used as a carbon source and reductive power to ultimately produce various value products, and especially alcohols, aldehydes, and/or polyhydroxyalkanoates (e.g., polyhydroxybutyric acid, PHB). FIGS. 4A and 4B exemplarily and schematically illustrate one of the preferred aspects presented herein where $CO_2$ and reduction equivalents are consumed in the CBB cycle (Calvin-Benson-Bassham cycle, also known as reductive pentose phosphate cycle), preferably in *Ralstonia* spec. (e.g., *eutropha*). Here, the net input is three moles of $CO_2$, six moles of reduction equivalent, and 9 ATP to form with theoretical 100% conversion efficiency one mole of G3P (glyceraldehyde 3-phosphate), which can then be converted to form, for example, pyruvate that may be converted to ethanol (4A) or isobutyraldehyde (4B).

More specifically, three molecules of $CO_2$ are channeled through a series of enzymatic reactions that generate a variety of phosphorylated compounds, which when coupled to glycolysis, lead to the formation of a single molecule of pyruvate or acetyl-CoA. In further preferred aspects, the microorganism is genetically modified to express an enzyme activity that utilizes fructose-6-phosphate as a substrate and generates acetylphosphate, a phosphoenolpyruvate precursor, as a product. Enzymes expressing such activity frequently can utilize xylulose-5-phosphate as a substrate and can therefore potentially deplete the CBB cycle of ribulose-5-phosphate utilized in $CO_2$ capture.

The inventor has recently found that this depletion can be avoided by engineering the microorganism to overexpress enzymatic activity that utilizes ribulose-5-phosphate as a substrate to produce ribulose-1,5-diphosphate. This depletes ribulose-5-phosphate, which in turn depletes ribose-5-phosphate, which has the effect of shifting the equilibrium of the reversible transformation between ribose 5-phosphate and xylulose-5-phosphate towards the formation of ribose-5-phosphate. This combination provides an alternate CBB pathway that utilizes the fixation of two molecules of $CO_2$ to produce 1 molecule of acetylCoA, compared to 3 molecules of $CO_2$ via the native CBB cycle, thereby improving the efficiency of $CO_2$ conversion into value-added products otherwise derived from PEP (and/or other 2 carbon metabolites derived from the CBB cycle) at least conceptually from 66% to 100%. Additionally, or alternatively, the inventors also discovered that where cultivation conditions were selected such that the intracellular PEP level is at or below 2 mM (e.g., where nitrogen is present at or below 3 mM in the medium), $CO_2$ fixation and concomitant value product formation is favored. Moreover, the inventor has also noted that the effect of the undesirable xylulose 5-phosphate activity of phosphoketolase can be reduced or even eliminated through overexpression of phosphoribulokinase, an enzyme of the CBB cycle that catalyzes the formation of ribulose 1,5-biphosphate from ribulose 5-phosphate (xylulose-5-phosphate is in equilibrium with ribose 5-phosphate). Overexpression of phosphoribulokinase results in depletion of ribulose 5-phosphate, which in turn leads to depletion of ribose 5-phosphate. This depletion of ribose 5-phosphate shifts the equilibrium between ribose 5-phosphate and xylulose 5-phosphate. This reduces the amount of xylulose 5-phosphate available to act as a substrate for phosphoketolase, effectively reducing this activity (i.e. through substrate competition) while not impacting the production of ribulose 1,5-bisphosphate necessary for $CO_2$ fixation. Such overexpression can reduce the apparent xylulose-5 phosphate activity of a phosphoketolase by 50% or more relative to the activity observed in a similar organism that does not overexpress phosphoribulokinase.

Additionally, it is contemplated that the CBB cycle may be further modified by recombinant expression of phosphoketolase to thereby generate acetylphosphate from an intermediate of the CBB cycle. The so formed acetylphosphate can then be converted in the microorganism acetyl-CoA, that is then used in the cell to produce a value added compound. Further suitable modifications and implications of a modified CBB cycle are described in U.S. 61/933,422, filed 30 Jan. 2014, which is incorporated by reference herein.

Figure 5A:
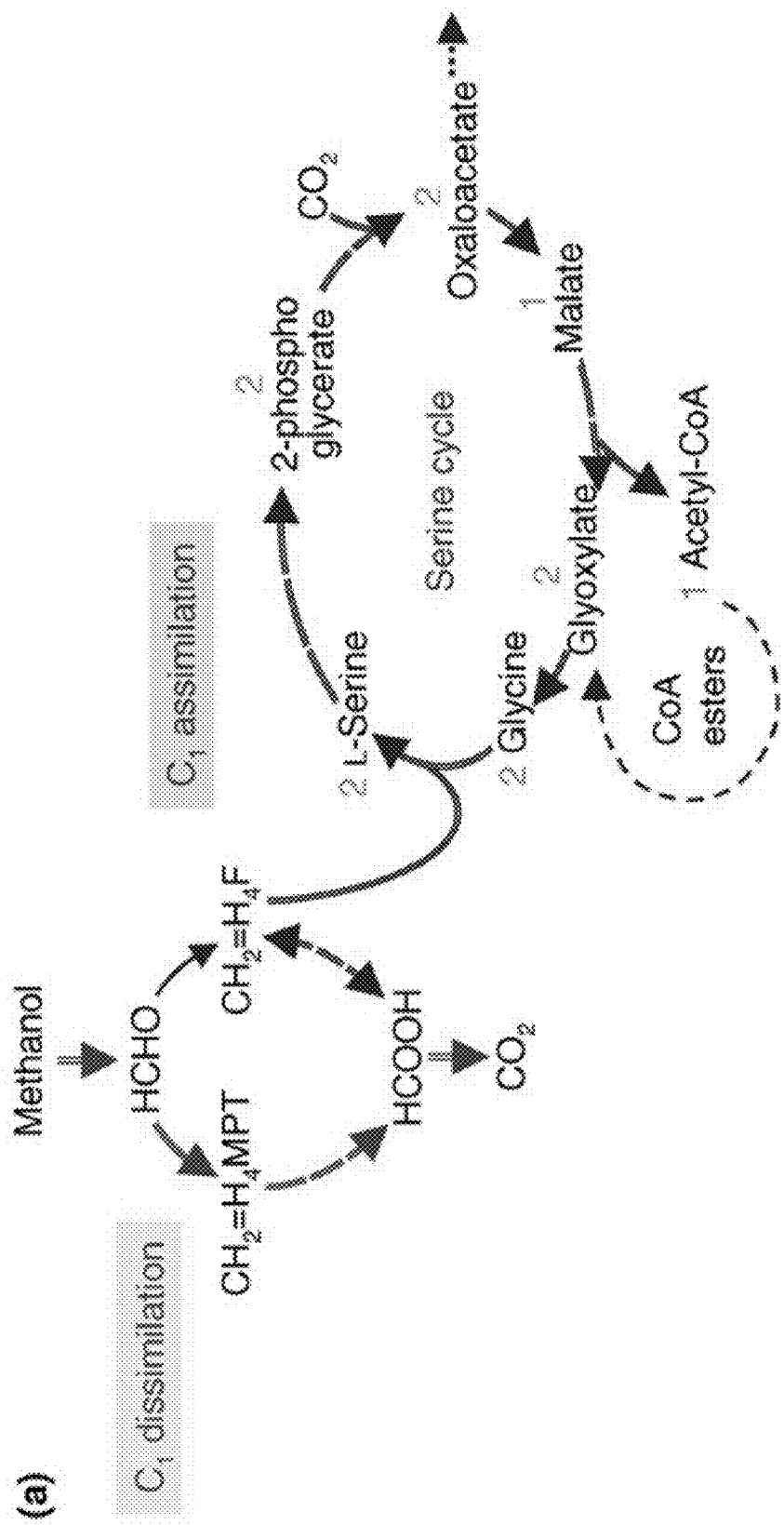
FIGS. 5A and 5B are exemplary schematics for C1-fixation via formaldedhyde and use of the serine cycle or RuMP cycle.
Figure 5B:
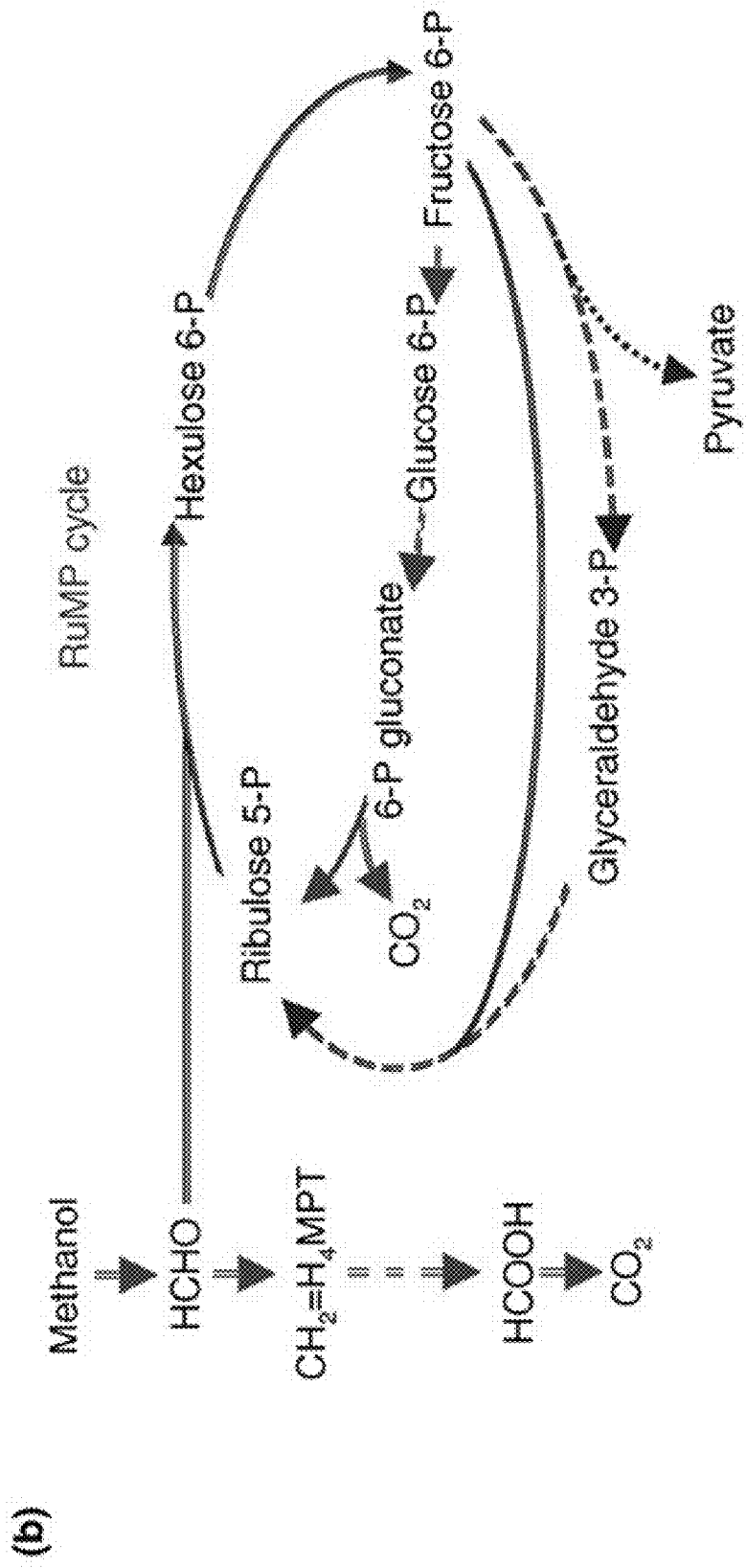

In yet further contemplated aspects of the inventive subject matter, it should be noted that microorganisms may also utilize methanol oxidation intermediates for value product production, and especially formaldehyde for C1 fixation to the value products. Of course, it should be appreciated that such fixation capabilities can be native to the microorganism, or due to a genetically engineered metabolic pathway. For example, especially suitable C1 fixation pathways using formaldehyde include the serine cycle and RuMP cycle (ribulose monophosphate cycle). A simplified schematic for the tie-in of methane oxidation with the serine cycle is shown in FIG. 5A while simplified schematic for the tie-in of methane oxidation with the RuMP cycle is shown in FIG. 5B. As noted before, it should be appreciated that all of the enzymatic activities needed for such tie-ins can be either native to the microorganism or engineered into the microorganism via overexpression of genes encoding proteins with the required activities.

More specifically, and with further respect to the serine cycle in FIG. 5A, methane is oxidized in vivo (or less preferably in vitro) to methanol and subsequently oxidized in vivo to formaldehyde, which is assimilated as a C1 unit via 5-10-methylenetetrahydrofolate to the serine cycle. Similarly, and with respect to RuMP cycle in FIG. 5B, methane is oxidized in vivo (or less preferably in vitro) to methanol and subsequently oxidized in vivo to formaldehyde, which is a substrate for the 3-hexulose-6-phosphate synthase forming 3-hexulose-6-phosphate from ribulose 5-phosphate and formaldehyde. The so formed 3-hexulose-6-phosphate can then be fed to the glycolysis pathway via fructose 6-posphate that ultimately leads to the formation of pyruvate and/or acetylCoA.

Figure 6:
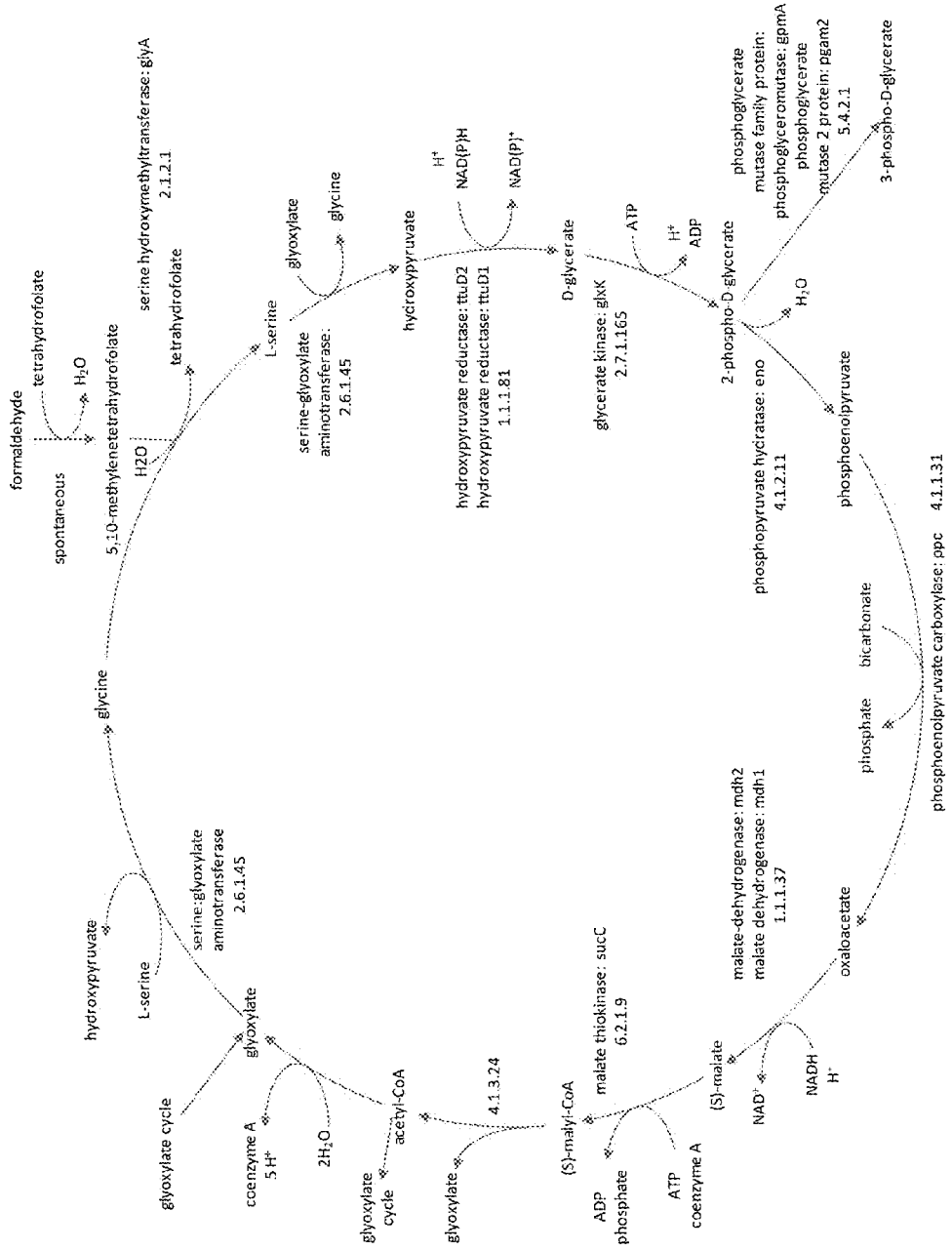
FIG. 6 is an exemplary schematic with detailed enzyme activities for the serine cycle.

FIG. 6 provides a more detailed illustration of the serine cycle, and it should be appreciated that all enzymatic steps in the serine cycle could be native (i.e., are part of the genetic/metabolic make-up of an unmodified microorganism) or that one or more steps needed for the cycle could be performed by an enzyme that is overexpressed and/or a recombinant enzyme. Similarly, FIGS. 7A and 7B schematically illustrate variants of the RuMP cycle, and it is once more noted that all enzymatic steps in the RuMP cycle could be native (i.e., are part of the genetic/metabolic make-up of an unmodified microorganism) or that one or more steps needed for the cycle could be performed by an enzyme that is overexpressed and/or a recombinant enzyme.

Figure 7A:
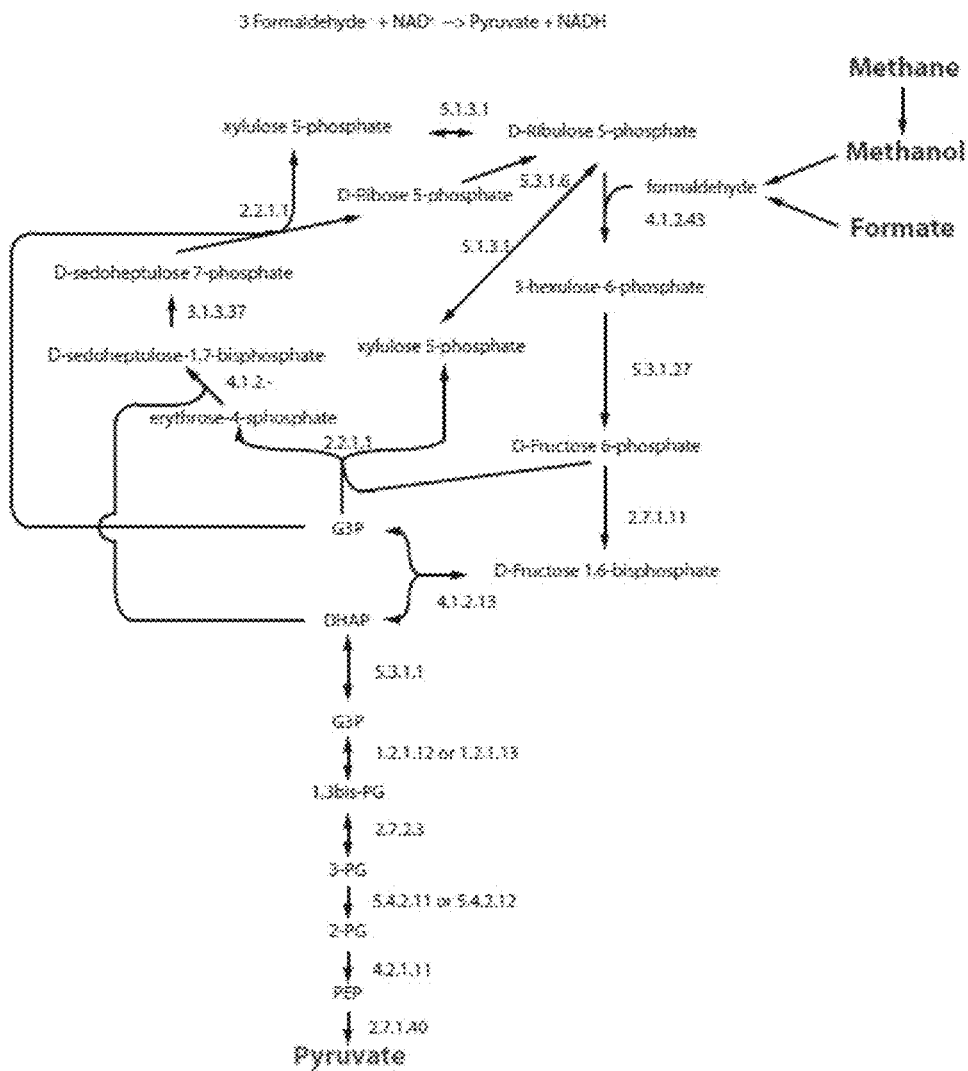
FIGS. 7A and 7B are exemplary schematic with detailed enzyme activities for the RuMP cycle.
Figure 7B:
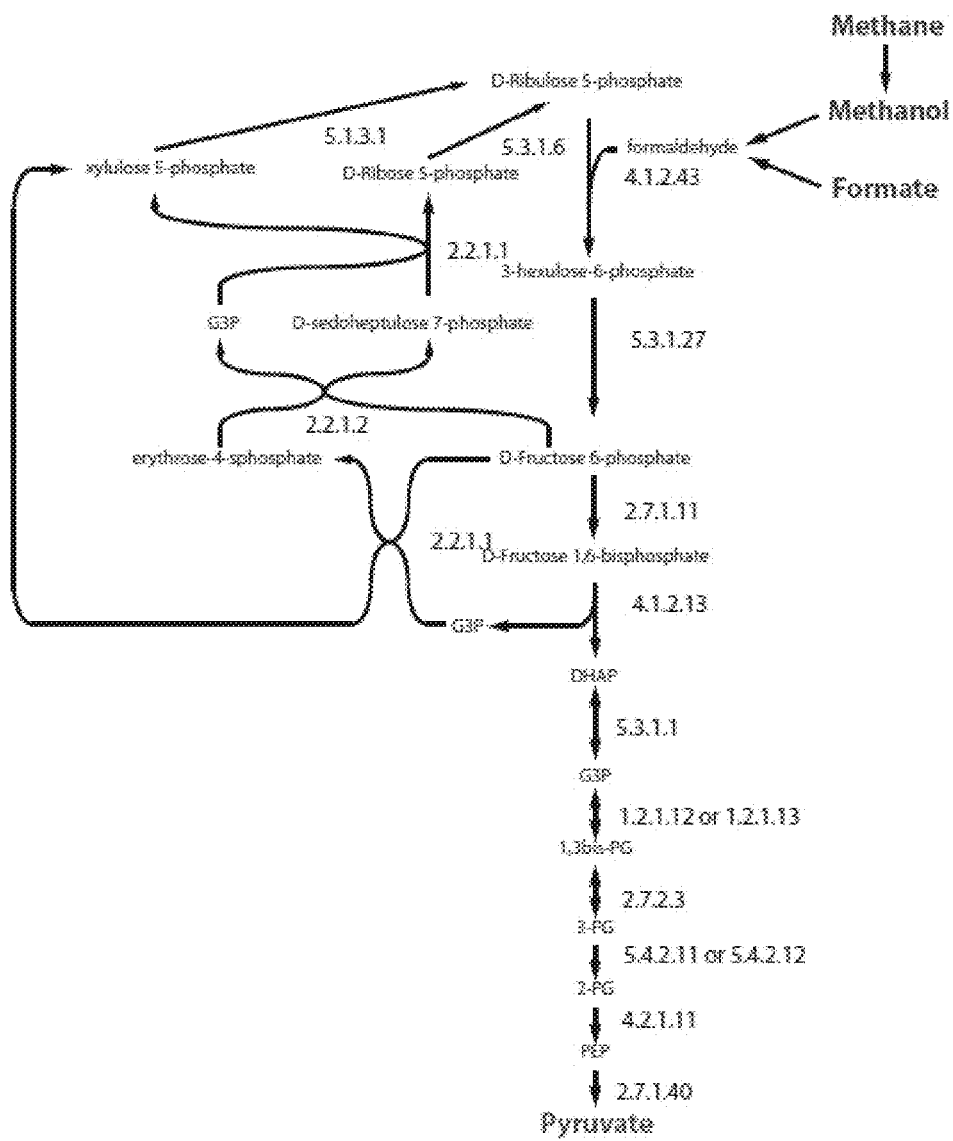

More specifically, and with further reference to FIGS. 7A and 7B, it should be recognized that $CO_2$ and reducing power can be obtained from formaldehyde (formaldehyde could be converted from methanol or formate). Viewed from a different perspective, the inventor contemplates energy efficient pathways to incorporate C1 substrates into pyruvate as building blocks for higher order alcohols and aldehyde. The common starting point to incorporate C1 compounds such as methane, methanol, and formic acid is formaldehyde. Condensation of formaldehyde with D-Ribulose 5-phosphate creates 3-hexulose-6-phosphate by 4.1.2.43 3-hexulose-6-phosphate synthase. 3 formaldehyde molecules have to be condensed with D-Ribulose 5-phosphate to create one pyruvate. The D-Ribulose 5-phosphate is recovered by recycling. 3-hexulose-6-phosphate is then transform to D-Fructose 6-phosphate by 5.3.1.27 6-phospho-3-hexuloisomerase. The D-Fructose 6-phosphate is then either part of the recycle or converted to D-Fructose 1,6-bisphosphate by 2.7.1.11 6-phosphofructokinase, which subsequently split into Dihydroxyacetone phosphate and D-Glyceraldehyde 3-phosphate by 4.1.2.13 fructose-bisphosphate aldolase. One Dihydroxyacetone phosphate is converted into D-Glyceraldehyde 3-phosphate by 5.3.1.1 triose-phosphate isomerase. D-Glyceraldehyde 3-phosphate is then phosporylated into 1,3-Bisphospho-D-glycerate by 1.2.1.12 glyceraldehyde-3-phosphate dehydrogenase or 1.2.1.13 glyceraldehyde-3-phosphate dehydrogenase (NADP+). 1,3-Bisphospho-D-glycerate transfers a phosphate to ADP to form ATP and 3-Phospho-D-glycerate by 2.7.2.3 phosphoglycerate kinase. The phosphate in 3-Phospho-D-glycerate is transferred to the second carbon to create 2-phospho-D-glycerate by 5.4.2.11 phosphoglycerate mutase (2,3-diphosphoglycerate-dependent) or 5.4.2.12 phosphoglycerate mutase (2,3-diphosphoglycerate-independent). Water is removed from 2-phospho-D-glycerate to produce phosphoenolpyruvate by 4.2.1.11 enolase. Finally phosphoenolpyruvate transfer a phosphate to ADP to form ATP and pyruvate by 2.7.1.40 pyruvate kinase. The remaining D-Glyceraldehyde 3-phosphate gets two carbons from one of the remaining D-Fructose 6-phosphate to create a 5-carbon ketose D-xylulose-5-phosphate and the aldose Erythrose-4-phosphate by 2.2.1.1 transketolase. The Erythrose-4-phosphate and the last D-Fructose 6-phosphate get converted into D-Glyceraldehyde 3-phosphate and sedoheptulose 7-phosphate by 2.2.1.2 transaldolase. The Glyceraldehyde 3-phosphate and sedoheptulose 7-phosphate undergoes a second transketolase to create a second D-xylulose-5-phosphate and one ribose-5-phosphate by 2.2.1.1 transketolase. The two D-xylulose-5-phosphate is converted back to D-Ribulose 5-phosphate by 5.1.3.1 ribulose-phosphate 3-epimerase and ribose-5-phosphate is converted into D-Ribulose 5-phosphate by 5.3.1.6 ribose-5-phosphate isomerase to recover all three D-Ribulose 5-phosphate used in the condensation reaction. The overall reaction is 3 formaldehyde+ PO₋₋ 42-+NAD++ADP-->Pyruvate+ATP+NADH+H+.

With respect to the microorganism it should be appreciated that the particular nature of the microorganism may change considerably. However, it is generally preferred that the microorganism is a strictly aerobic microorganism. In other aspects, the microorganism may also be a facultative aerobic microorganism, and in some aspects also a facultative anaerobic (or strictly anaerobic) microorganism. Thus, suitable microorganisms will include various bacteria, cyanobacteria, or fungi, and non-photosynthetically active microorganisms are particularly preferred. Therefore, in some embodiments, the microbial cells belong to a genus selected from the group consisting of *Escherichia, Corynebacterium, Clostridium, Zymonomas, Salmonella, Rhodococcus, Pseudomonas, Bacillus, Lactobacillus, Enterococcus, Alcaligenes, Klebsiella, Paenibacillus, Arthrobacter, Brevibacterium, Pichia, Candida, Hansenula, Synechococcus, Synechocystis, Anabaena, Ralstonia, Methylobacterium, Methanobacterium, Lactococcus* and *Saccharomyces*.

Therefore, suitable microorganisms may be *Escherichia coli, Corynebacterium glutamicum, Clostridium acetobutyricum, Clostridium beijerinckii, Alcaligenes eutrophus, Bacillus subtilis, Bacillus licheniformis, Zymonomas mobilis, Paenibacillus macerans, Rhodococcus erythropolis, Pseudomonas putida, Lactobacillus plantarum, Enterococcus faecium, Enterococcus gallinarium*, and *Enterococcus faecalis, Synechococcus elongates, Synechocystis* sp., *Anabaena* sp., *Ralstonia eutropha, Methylobacterium mesophilicum, Methylobacterium adhaesivum; Methylobacterium aminovorans; Methylobacterium aquaticum; Methylobacterium chloromethanicum; Methylobacterium dichloromethanicum; Methylobacterium extorquens; Methylobacterium fujisawaense; Methylobacterium hispanicum; Methylobacterium isbiliense; Methylobacterium lusitanum; Methylobacterium mesophilicum; Methylobacterium nodulans; Methylobacterium organophilum; Methylobacterium podarium; Methylobacterium populi; Methylobacterium radiotolerans; Methylobacterium rhodesianum; Methylobacterium rhodinum; Methylobacterium suomiense; Methylobacterium thiocyanatum; Methylobacterium variabile; Methylobacterium zatmanii; Methanobacterium bryantii, Methanobacterium formicu, Methanobrevibacter arboriphilicus, Methanobrevibacter gottschalkii, Methanobrevibacter*

*ruminantium, Methanobrevibacter smithii, Methanocalculus chunghsingensis, Methanococcoides burtonii, Methanococcus aeolicus, Methanococcus deltae, Methanococcus jannaschii, Methanococcus maripaludis, Methanococcus vannielii, Methanocorpusculum labreanum, Methanoculleus bourgensis, Methanoculleus marisnigri, Methanofollis liminatans, Methanogenium cariaci, Methanogenium frigidum, Methanogenium organophilum, Methanogenium wolfei, Methanomicrobium mobile, Methanopyrus kandleri, Methanoregula boonei, Methanosaeta concilii, Methanosaeta thermophile, Methanosarcina acetivorans, Methanosarcina barkeri, Methanosarcina mazei, Methanosphaera stadtmanae, Methanospirillium hungatei, Methanothermobacter defluvii, Methanothermobacter thennautotrophicus, Methanothermobacter thermoflexus, Methanothermobacter wolfei, Methanothrix sochngenii, Lactococcus lactis* and *Saccharomyces cerevisiae.*

It should further be appreciated that the microorganism contemplated herein will generally be capable of using a gaseous substrate as carbon source without genetic modification, but may also be engineered to impart capability of using or to use a specific gaseous substrate (and especially methane, syngas, or a mixture of $CO_2$: CO: $H_2$ at any ratio). For example, engineered microorganisms contemplated herein will be able to convert methane to formaldehyde and gain reduced NAD(P)H through this process, wherein (a) the formaldehyde can be fixed directly or (b) can be converted to $CO_2$ and NAD(P)H. In another example, the engineered microorganism may also be capable of converting syngas or a $CO_2$:CO:$H_2$ mixture to $CO_2$ and NAD(P)H, and fix $CO_2$.

Therefore, especially preferred microorganisms will comprise (naturally or via genetic engineering) one or more enzymes suitable for one or more of the following pathways: pyruvate to acetaldehyde by pyruvate decarboxylase; 2-ketobutyrate to propanal by 2-ketoisovalerate decarboxylase; linear carbon chain elongation using leuABCD genes; decarboxylation of one or more of 2-ketovalerate, 2-ketocaproate, 2-ketoheptanoate, 2-ketooctanoate, 2-keto-3-methylvalerate, 2-keto-4-methylcaproate, 2-keto-5-methylheptanoate, 2-keto-6-methyloctanoate, 2-keto-isovalerate, 2-ketoisocaproate, 2-keto-5-methylhexanoate, or 2-keto-6-methylocatnoate by kivd; branched carbon chain elongation of 2-ketobutyrate to 2-keto-3-methylvalerate using ilvGMCD or ilvBNCD; and branched carbon chain elongation of pyruvate to 2-keto-isovalerate using alsS and ilvCD or ilvIHCD genes.

Viewed from another perspective, the microorganisms comprise one or more native or recombinant active enzymes from one or more of the following pathways: methane to methyl-CoM; methyl-CoM to 5-methyl-THMPT; 5-methyl-THMPT to 5,10-methyl-THMPT; 5,10-methyl-THMPT to Formaldehyde; methane to methanol; methanol to formaldehyde; formaldehyde to formic acid; formic acid to carbon dioxide; carbon monoxide to carbon dioxide; hydrogen and oxidized NAD(P)+ to reduced NAD(P)H and proton. Consequently, and viewed from a different perspective, contemplated microorganisms may also have a native and/or recombinant active enzyme selected from the group consisting of an acetyl-CoA acetyltransferase, an 3-hydroxyacyl-CoA dehydrogenase, a crotonyl-CoA hydratase, a butyryl-CoA dehydrogenase, a trans-enoyl-CoA reductase and a butanal dehydrogenase.

In certain cases, the microorganism will also have a reduced activity of one or more enzymes capable of modifying the specific chemical produced, and most typically a reduced or eliminated activity for alcohol and/or aldehydes (other than formaldehyde) dehydrogenase activity. Thus, contemplated microorganisms may have (naturally or via genetic modification) reduced activity of one or more native alcohol dehydrogenases to block the conversion of specific C3-C8 aldehyde into corresponding C3-C8 alcohols compared to unmodified microorganism. Therefore, preferred products include alcohols such as ethanol, 1-propanol, 1-butanol, isobutanol, 1-pentanol, 1-hexanol, 1-heptanol, 1-octanol, 2-methyl-1-propanol, 3-methyl-1-butanol, 4-methyl-1-pentanol, 2-methyl-1-butanol, 3-methyl-1-pentanol, and 4-methyl-1-hexanol. Likewise, preferred products include aldehydes such as acetaldehyde, 1-propanal, 1-butanal, 1-pentanal, 1-hexanal, 1-hexanal, 1-heptanal, 1-octanal, 2-methyl-1-propanal, 3-methyl-1-butanal, 4-methyl-1-pentanal, 2-methyl-1-butanal, 3-methyl-1-pentanal, and 4-methyl-1-hexanal; and carboxylic acids (which may also be keto- or hydroxy acids) such as acetate, lactate, n-butyric acid, isobutyric acid.

With further respect to reduced activities of particular enzymes (and especially alcohol dehydrogenases), it is generally preferred that the activity is reduced via deletion, knock-down, or knock-out mutations (e.g., via antisense RNA or siRNA, gene disruption, etc.). For example, expression (transcription and/or translation) of one or more endogenous alcohol dehydrogenase activity will be at least decreased, and more preferably suppressed, and it should be noted that in especially preferred aspects, all or almost all of the alcohol dehydrogenases will be suppressed or deleted. For example, suppressed or deleted dehydrogenases include adhE, IdhA, frdB, and pflB. Likewise, it is contemplated that one or more aldehyde dehydrogenases (other than formaldehyde dehydrogenase) will be deleted, especially where the desired value product is an C2+aldehyde.

Of course, it should be recognized that all of the genes encoding the desired enzymatic activity may be unmodified or may be engineered to impart a desired selectivity, an increased turnover rate, etc. (see e.g., Proc. Nat. Acad. Sci. (2008), 105, no. 52: 20653-20658; or WO2009/149240A1). Suitable genes for the above and further activities of the metabolically engineered cells are well known in the art, and use of all of those in conjunction with the teachings presented herein is deemed suitable. Moreover, all of the known manners of making metabolically engineered cells are deemed suitable for use herein. For example, metabolically engineered cells may modified by genomic insertion of one or more genes, operons, and/or transfection with plasmids or phagemids as is well known in the art. In some embodiments, a mutant microorganism may also be used in the methods of the present invention, and may be further modified recombinantly as desired.

Viewed from a different perspective, recombinant microorganism may be prepared using all methods known to one of ordinary skill in the art, and it will be understood that modifications may include insertion or deletion of one or more genes as deemed necessary to increase or decrease activity of a particular enzymatic pathway. Thus, suitable modifications will include random mutagenesis to produce deficient expression patterns, extrachromosomal (typically plasmids or phagemid) nucleic acids with suitable control elements to produce controlled overexpression of one or more enzymes, genomic insertions with suitable control elements to produce controlled overexpression of one or more enzymes, etc.

For example, suitable energetic low-molecular weight gas include raw or processed or purified syngas streams from gasification operations, which may or may not have undergone a shift reaction, recycle gas streams in gas processing operations (and especially gasification operations), off gases or purge gases from pressure swing adsorption units, catalytic and non-catalytic hydrogenation operations, hydrocracking operations, etc., all of which may be combined with CO and $CO_2$ rich gas streams that may be derived from numerous sources, including combustion units, coking units, catalyst regenerators, etc. Moreover, suitable energetic low-molecular weight gas may also be derived from landfill operations, gasification and reliquefaction operations, natural gas receiving and processing terminals, etc. Still further, contemplated energetic low-molecular weight gas may also be obtained from solid or liquid adsorbent compositions as well as cryogenic operations.

Therefore, and viewed from a different perspective, suitable energetic low-molecular weight gases will comprise CO, $CO_2$, and/or $CH_4$ in an amount of at least 2-5 vol %, more typically between 5-10 vol %, even more typically between 10-30 vol %, and most typically between 30-50 vol % and even more. Likewise, the hydrogen concentration may vary considerably and will generally be at least 0.5-5 vol %, more typically between 5-10 vol %, even more typically between 10-30 vol %, and most typically between 30-50 vol % and even more. In addition, suitable media will also include additional non-gaseous carbon sources as desired. For example, appropriate additional carbon sources include various saccharides, and particularly glucose, fructose, sucrose, starch, cellulose, hemicellulose, glycerol, carbon dioxide, protein and fragments thereof, and/or amino acids. Exemplary further carbon sources include lipids, proteins, complex organic mixtures (e.g., biosolids, meat processing waste products, plant based materials, etc).

The flow rate of the energetic low-molecular weight gas will typically be well above the rate required to obtain saturation of the energetic low-molecular weight gas in the medium. Thus, suitable flow rates will result in bubble formation in the medium, which may be vigorous enough to drive of volatile reaction products from the microorganism. Therefore, in especially preferred aspects of the inventive subject matter, preferred flow rates will be between 0.5-1.0 vvm, more typically between 1.0-1.5 vvm, and even more typically between 1.5-3.0 vvm.

It should further be appreciated that the culture conditions will typically depend on the particular choice of microorganism, and the person of ordinary skill in the art will be readily able to choose the appropriate medium. Among other suitable choices, it is generally preferred that the carbon source in the medium is provided to at least some degree (e.g., at least 30%, more typically at least 50%, most typically at least 75%), and more typically substantially entirely (e.g., at least 90%, more typically at least 90%, most typically at least 95%) provided in gaseous form from an energetic low-molecular weight gas. Most preferably, the energetic low-molecular weight gas is or comprises methane, ethane, syngas, or modifications thereof, or any gas that provides a net exothermic reaction when combusted with oxygen and in which the largest volatile component has a molecular weight of less than 100 Da. Moreover, it is noted that in at least some aspects of the inventive subject matter the microorganism is grown and used to produce value product under aerobic conditions, which is typically not advised due to the nature of the energetic gases. However, it should be appreciated that the gas composition may be controlled such that aerobic growth is promoted while reducing or avoiding conditions that favor autoignition or explosion.

Regardless of the particular culture condition, it is especially preferred that the reaction products produced by the microorganism are removed in the gas phase where the reaction product is a volatile compound (e.g., butyraldehyde). More preferably, such removal will be performed in a continuous fashion during cell culture, and removal may be based on agitation of the fermentation medium, stripping the fermentation medium with an inert gas, stripping the fermentation medium with an oxygen containing gas, and/or temporarily binding the aldehyde to a binding agent. For example, suitable gases used in the gas stripping process may be methane, syngas, air, nitrogen, ammonia, carbon dioxide, carbon monoxide, hydrogen, oxygen, and all reasonable combinations thereof combinations thereof. Alternatively, aldehyde removal may also be performed after fermentation, or in a semi-continuous manner (e.g., by intermittent contact with stripping gas). Once driven off the fermentation medium, various methods may be used to recover the reaction product, including trapping in solution, by dissolution or adsorption into solvent, or via adsorption onto a solid sorbent. The so recovered product may then be sold as a commodity or converted to a desirable product via oxidation, reduction, or condensation.

Alternatively, and especially where the reaction product is not sufficiently volatile to be removed in meaningful quantities from the medium, the reaction product may be removed from the liquid phase. Thus, and depending on the production kinetics, removal may be performed on-line from a continuous fermentation, or intermittently from batch fermentation. Among other suitable removal methods, preferred methods include distillation, differential solubilization in solvents immiscible with the culture medium, adsorption using specific or non-specific solvents, etc. Consequently, it should also be appreciated that the type of fermentation system may vary considerably, and appropriate fermentation systems include batch fermentors, continuous fermentors, and fermentors with a solid phase (e.g., hollow-fiber reactors, etc.) that retain the microorganisms.

For example, in one especially preferred aspect of the inventive subject matter, the microorganism is *Ralstonia eutropha* and is cultured in an appropriate liquid medium using syngas having a molar ratio of $H_2$ to CO of about 3 to 1 at a feed rate of about 1.5-2.5 vvm under aerobic culture conditions. Most typically, the syngas is a raw syngas from a steam hydrogasification and/or steam reforming operation in which biomass is converted to the syngas. Thus, the syngas will also include further non-energetic and inert components. In particularly preferred embodiments, the feed gas is not only used to provide a carbon source and hydrogen to the microorganism, but is also used at a rate effective to sparge out desired products from the liquid phase in which the microorganisms grow. Alternatively, or additionally, desired products can also be extracted from the liquid phase.

Consequently, it should be appreciated that using contemplated systems and methods one can use industrial byproducts (e.g., $CO_2$ or methane) as raw material to produce value-added products. Most typically, $CO_2$ and methane can be converted to formic acid or formaldehyde, and *Ralstonia eutropha* (or other suitable microorganism) can be used to convert formic acid or formaldehyde to polymers, bulk chemicals and pharmaceutical intermediates. It should be particularly noted that such process does generally not rely on the relatively slow photosynthetic process to fix $CO_2$, and therefore has a much higher $CO_2$ fixation rate compared with all plant- or algae-based $CO_2$ fixation processes. Current biomass productions by plants or algae require a large area of agricultural land, moderate temperature and constant light distribution. Contemplated processes exploit *Ralstonia*'s $CO_2$ fixation rate (0.4 g/L/day according to Ishizaki et al., 2001, equivalent to 400 g/m²/day in a 1 m high bioreactor), which is significantly higher than plant- or algae-based $CO_2$ fixation processes (2 g/m²/day and 50 g/m²/day, respectively), which rely on the slow process of photosynthesis (Zhu et al., 2008). Using a continuous fermentation, a metabolically engineered *Ralstonia* could produce 2 g/L/day biomass in which 30% of the dry weight is PHA and 50% of the dry weight is protein. Since there is little chance that any other microorganism could grow in formic acid, there is no concern of contamination which is a common problem for other fermentation industries. When an open pond or closed bioreactor is used, a metabolically engineered *Ralstonia* could fix over 400 g/m²/day $CO_2$ assuming the depth of the open pond is 1 m, or could fix over 4000 g/m²/day $CO_2$ assuming the depth of a bioreactor is 10 m.

Further considerations, methods, and compositions suitable for use herein are described in U.S. Pat. No. 7,851,188 and in International applications with the serial numbers PCT/US 12/29013 (published as WO2012/125688) and PCT/US 12/63288 (not yet published), all of which are incorporated by reference herein.

Thus, specific embodiments and applications of methods of microbial production of fuel components from low-molecular weight gas mixtures have been disclosed. It should be apparent, however, to those skilled in the art that many more modifications besides those already described are possible without departing from the inventive concepts herein. The inventive subject matter, therefore, is not to be restricted except in the spirit of the appended claims.

What is claimed is:

1. A method of producing a value product, comprising:
providing methane, and using a genetically engineered microorganism to convert the methane into reduction equivalents and $CO_2$ or formaldehyde, wherein the microorganism is engineered to express at least one recombinant gene that encodes an enzyme (1) that has an activity selected from the group consisting of methane monooxygenase, alcohol dehydrogenase, and formaldehyde dismutase, or (2) that catalyzes at least one step in a methane oxidation pathway;
wherein the microorganism is further genetically modified to have reduced or abrogated activity for at least one of aldehydes dehydrogenase and alcohol dehydrogenase;
using a Calvin-Benson-Bassham cycle (CBB) cycle, a serine cycle, or a ribulose monophosphate cycle (RuMP) cycle in the microorganism to produce the value product via assimilation of the $CO_2$ or formaldehyde, and wherein the value product is an aldehyde, an alcohol, or a polyhydroxyalkanoate.

2. The method of claim 1 wherein the microorganism is engineered to express at least two recombinant genes that encode an enzyme having an activity selected from the group consisting of methane monooxygenase, alcohol dehydrogenase, and formaldehyde dismutase.

3. The method of claim 1 wherein the at least one recombinant gene encodes at least one enzyme that catalyzes at least one step in a conversion of methane into $CO_2$ and that generates the reduction equivalents during the conversion of the methane to the formaldehyde.

4. The method of claim 3 wherein the microorganism is engineered to express at least one recombinant gene that encodes an enzyme having an activity selected from the group consisting of factor F420-reducing hydrogenase, F420-dependent methylene-H4SPT dehydrogenase, heterodisulfide reductase, methyl-coenzyme M reductase, methyl-H4MPT:coenzyme M methyltransferase complex, F420-dependent methylene-H4SPT reductase, 5,6,7,8-tetrahydromethanopterin hydro-lyase (formaldehyde-activating enzyme), and formaldehyde dehydrogenase.

5. The method of claim 1 wherein the microorganism is genetically engineered to express at least one recombinant gene in the CBB cycle, the serine cycle, or the RuMP cycle.

6. The method of claim 1 wherein the value product is an aldehyde, or an alcohol.

7. The method of claim 1 wherein the microorganism is an aerobic microorganism, and wherein the aerobic microorganism is cultivated under aerobic conditions.

8. The method of claim 1 wherein the microorganism is an aerobic microorganism that is genetically modified to grow under anaerobic conditions.

9. The method of claim 1 wherein the microorganism belongs to the genus of *Ralstonia*.

* * * * *